United States Patent [19]

Anderson et al.

[11] 4,359,474

[45] Nov. 16, 1982

[54] 1-PHENYL-PYRAZOLE DERIVATIVES AS GLUCAGON INHIBITORS

[75] Inventors: Paul L. Anderson, Dover; Nicholas A. Paolella, Livingston, both of N.J.

[73] Assignee: Sandoz, Inc., East Hanover, N.J.

[21] Appl. No.: 211,361

[22] Filed: Nov. 28, 1980

[51] Int. Cl.³ .......................................... A61K 31/415
[52] U.S. Cl. ................................................ 424/273 P
[58] Field of Search ................................... 424/273 P

[56] References Cited

U.S. PATENT DOCUMENTS 4,220,792  9/1980  Anderson et al. ............... 424/273 P

FOREIGN PATENT DOCUMENTS 1368615  10/1974  United Kingdom ............ 424/273 P

OTHER PUBLICATIONS

*J. of Med. Chem.*, vol. 7, (1964), pp. 102–107.

*Primary Examiner*—Frederick E. Waddell
*Attorney, Agent, or Firm*—Gerald D. Sharkin; Robert S. Honor; Joseph J. Borovian

[57] ABSTRACT

The invention discloses certain 1-phenyl-pyrazole derivatives having pharmacological activity in animals and useful as glucagon inhibiting agents. Nearly all of the compounds of this invention are prepared by cyclization of a phenyl hydrazine compound with a 1,1,3,3-tetra-$C_{1-4}$-alkoxy-propane compound.

10 Claims, No Drawings

1-PHENYL-PYRAZOLE DERIVATIVES AS GLUCAGON INHIBITORS

The present invention relates to the use of certain 1-phenyl pyrazole derivatives, and the pharmaceutically acceptable acid addition salts thereof, where such may exist, as glucagon-inhibiting agents.

British Pat. No. 1,368,615 discloses certain pyrazole derivatives useful as analgesic and anti-inflammatory agents. In addition, J. of Med. Chem. 7 pp. 102–105 (1964) is directed to an investigation of the antidiabetic activity of certain pyrazole compounds.

The present invention involves the novel use of the compounds of formula I:

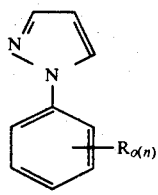

wherein
$R_o$ is methyl, trifluoromethyl or amino, and
n is 1 or 2,
and the pharmaceutically acceptable acid addition salts thereof, with the proviso that when n is 2, $R_o$ is methyl, one methyl group being in the 2-position of the phenyl ring and the other methyl group being in the 3- or 4-position of the phenyl ring.

Preferred compounds of formula I are compounds wherein n is 1 and $R_o$ is trifluoromethyl, methyl in the 2-position of the phenyl ring or amino in the 2-position of the phenyl ring, and the pharmaceutically acceptable acid addition salts thereof. The more preferred compounds of formula I are compounds wherein n is 1 and $R_o$ is trifluoromethyl and the compound wherein n is 1 and $R_o$ is methyl in the 2-position of the phenyl ring. The most preferred compound of formula I is 1-o-tolyl-1H-pyrazole.

All of the compounds of formula I, save for compounds wherein $R_o$ is amino, may be prepared by cyclization of a phenyl hydrazine compound of formula II:

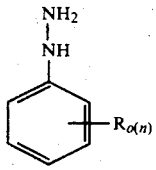

wherein $R_o$ is methyl or trifluoromethyl, and n is 1 or 2, with the proviso as set forth above, with a 1,1,3,3-tetra-$C_{1-4}$-alkoxypropane compound. The cyclization may be effected by processes known per se for the cyclization of hydrazine compounds. Preferably, the cyclization involves reacting a compound of formula II, as described above, with a 1,1,3,3-tetra-$C_{1-4}$-alkoxypropane, more preferably, a 1,1,3,3-tetra-$C_{1\ or\ 2}$alkoxypropane compound, in the presence of an inert, organic solvent such as the lower alkanols, e.g., methanol, ethanol, and the like, and an inorganic mineral acid such as sulfuric acid, hydrochloric acid and the like, in concentrated form. The cyclization is conveniently carried out at temperatures of between 50° C. and 100° C., preferably, between 80° C. and 90° C. Reaction times will, of course, vary but it is preferred that the reaction be conducted for a period of 1 to 4 hours, more preferably, for 2 to 3 hours.

The compounds of formula I wherein $R_o$ is amino may be prepared by a two-step reaction comprising, in a first step, the cyclization of a compound of formula III:

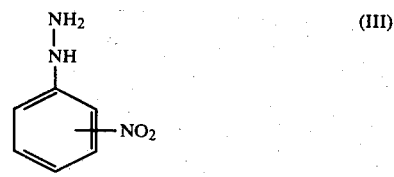

essentially as described above, to obtain the corresponding ortho-, meta- or para-nitrophenyl pyrazole compound which, in a second step, is catalytically hydrogenated to obtain the desired amino compound of formula I. Thus, the corresponding ortho-, meta- or para-nitrophenyl pyrazole compound is reduced in the presence of hydrogen gas under pressure and in the presence of a catalyst such as palladium on carbon or platinum oxide on carbon. The reaction is carried out in the presence of an inert, organic solvent such as the lower alkanols, e.g., methanol, ethanol, and the like. The temperature of the reaction is not critical, but it is preferred that the reaction be run at temperatures from about 10° C. to 80° C., more preferably, from about 20° C. to 50° C. Reaction times will, of course, vary but it is preferred that the reaction be conducted for a period of 1 to 24 hours, more preferably, for 16 to 20 hours.

It will be noted that the above-identified compounds of formula I wherein $R_o$ is amino bear a free amino group and can, therefore, form pharmaceutically acceptable acid addition salts; it being understood that the use of such salts is comprehended as being included within the scope of the present invention.

The products of the above-described reactions may be recovered and purified in conventional manner, e.g., by crystallization, distillation or chromatographic techniques, such as eluting from a chromatographic column or separating on a silica layer.

Many of the compounds of formulae II and III are either known and obtained by methods described in the literature, or where not known, may be obtained by methods analogous to those described in the literature.

As previously indicated, pharmaceutically acceptable acid addition salts (i.e., those salts which do not significantly increase the toxicity of the basic compound) of the compounds of formula I, where such may exist, are included within the scope of this invention. Included are salts with inorganic acids, e.g., the hydrochloride, hydrobromide, hydroiodide, phosphate (including hydrogen phosphates) metaphosphate, sulfates (including hydrogen sulfate) and perchlorate salts.

The compounds of formula I, and their pharmaceutically acceptable acid addition salts, are useful as glucagon inhibiting agents in the treatment of diabetes as indicated by a lowering of plasma glucagon levels in alloxan diabetic rats. Adult male rats, each weighing between 200 and 400 g., are injected intravenously with 50–100 mg./kg. of alloxan and, after 5 days, are tested for the presence of urinary glucose (Clinistix). The selection of animals is determined according to the degree of urine Clinistix reaction, i.e., only animals with a positive urine response (deep purple color of Clinistix within 15 seconds) are used. The rats are divided into two groups, viz., the "insulin" group, wherein the rats are intramuscularly administered 1 unit/kg. body weight of insulin and the "test compound" group, wherein the rats are dosed orally with 100 mg./kg. body weight of the test compound. After two hours, the animals in each group are sacrificed and 2 to 5 mls. of blood are collected and the plasma separated. The plasma is stored frozen until assayed for glucagon, at which time plasma levels of glucagon are determined using radioimmunological techniques. Similar tests are run simultaneously with a "negative control" group comprising non-diabetic rats which received only the alloxan.

For the above-mentioned use, the compounds of formula I and their pharmaceutically acceptable salts may be administered orally or parenterally as such or admixed with conventional pharmaceutical carriers. They may be administered orally in such forms as tablets, dispersible powders, granules, capsules, syrups and elixirs, and parenterally as solutions, e.g., a sterile injectable aqueous solution. The compositions for oral use may contain one of more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl-p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier or adjuvant.

The precise dosage of a compound of formula I, or a pharmaceutically acceptable acid addition salt thereof, to be employed depends upon several factors including the severity of the condition being treated, the mode of administration and the particular compound employed. However, in general, satisfactory results in lowering the glucagon level in plasma are obtained when a compound of formula I, or a pharmaceutically acceptable acid addition salt thereof, is administered at a daily dosage of from about 50 milligrams to about 300 milligrams per kilogram of animal body weight, preferably given orally and in divided doses three times a day, more preferably, before each meal, or in sustained release form. For most large mammals, the total daily dosage is from about 250 milligrams to about 3000 milligrams. Unit dosage forms suitable for internal use comprise from about 50 milligrams to about 3000 milligrams, more usually 50 to 1500 milligrams of the active compound in intimate admixture with a solid or liquid, pharmaceutically acceptable carrier.

A representative formulation suitable for oral administration three times a day, preferably before each meal, for lowering the glucagon level is a capsule prepared by standard encapsulating techniques which contains the following:

| Ingredients | Weight (mg.) |
| --- | --- |
| 1-o-tolyl-1H—pyrazole | 100 |
| inert solid diluent (e.g., starch, lactose, kaolin, etc.) | 200 |
| Total | 300 |

The following examples are for purposes of illustration only and are not intended to in any way limit the scope of the invention.

EXAMPLE 1

1-o-tolyl-1H-pyrazole

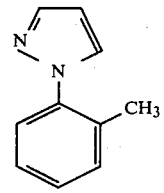

Into a 1 liter, 2-neck flask, fitted with a condenser and a magnetic stirrer, is successively added 90.0 g. (0.570 M.) of o-tolyl-hydrazine hydrochloride hydrate, 100 ml. of water, 63 ml. of 100% ethanol and 139.0 g. (0.633 M.) of 1,1,3,3-tetraethoxypropane. The reaction mixture is then heated slowly to between 80° C. and 90° C., and after maintaining the mixture at this temperature range for a period of about 3 hours, the reaction mixture is quenched on ice water and extracted with ethylacetate/ether. After drying the organic solution over anhydrous sodium sulfate, the solvents are evaporated to obtain a very dark liquid. Distillation in an air oven at a temperature between 110°–120° C. and a pressure of 1 mm. of Hg. yielded a light yellow oil (Yield: 83%).

Diabetic rat test -60%-100 mg./kg. (aver. of 4 runs)

EXAMPLE 2

1-(m-trifluoromethylphenyl)-pyrazole

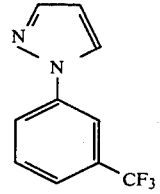

Into a 500 ml., 2-neck flask, fitted with a condenser and a magnetic stirrer, is successively added 35.2 g. (0.2 M.) of m-trifluoromethylphenyl hydrazine, 15 ml. of water, 20 ml. of 100% ethanol, 16.5 ml. of concentrated hydrochloric acid (slowly) and 44.0 g. (0.2 M.) of 1,1,3,3-tetraethoxypropane. The reaction mixture is then heated slowly to between 80° C. and 90° C., and after maintaining the mixture at this temperature range for a period of between 2 and 3 hours, the reaction mixture is cooled, quenched on ice water, extracted with ethylacetate and washed several times with water. After drying the organic solution over sodium sulfate, the solvent is evaporated on a rotary evaporator to obtain a very dark liquid which is then distilled at 70° to 80° C. and a pressure of about 100 microns to yield a light yellow oil (Yield: 80%).

Diabetic rat test -62%-100 mg./kg. (aver. of 4 runs)

EXAMPLE 3

Following essentially the procedure of Example 2, and using in place of m-trifluoromethylphenyl hydrazine, an equivalent amount of:
 (a) p-tolyl hydrazine,
 (b) o-trifluoromethylphenyl hydrazine,
 (c) 2,4-dimethylphenyl hydrazine, or
 (d) 2,3-dimethylphenyl hydrazine,
there is obtained
 (a) 1-p-tolyl-1H-pyrazole, m.p. 30°-32° C.
   (Yield: 63%)
   -15%-100 mg./kg.
 (b) 1-(o-trifluoromethylphenyl)-pyrazole, an oil
   (Yield: 83%)
   -45%-100 mg./kg.
 (c) 1-(2,4-dimethylphenyl)-pyrazole, an oil
   (Yield: 76%)
   -25%-100 mg./kg. (aver. of 2 runs), and
 (d) 1-(2,3-dimethylphenyl)-pyrazole, an oil
   (Yield: 49%)
   -32.5%-100 mg./kg. (aver. of 3 runs), respectively.

EXAMPLE 4

1-(o-aminophenyl)-pyrazole

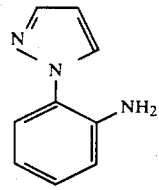

Into a Parr hydrogenation apparatus is successively added 20 g. (0.106 M.) of 1-(o-nitrophenyl)-pyrazole and 150 ml. of methanol and the resultant solution is hydrogenated in the presence of 1.0 g. of hydrogenation catalyst (10% Pd on active charcoal) at between 40 and 50 p.s.i. of hydrogen pressure at room temperature. After the theoretical uptake of hydrogen is achieved, the reaction mixture is filtered to remove the palladium and the solvent is removed on a rotary evaporator. Ether is then added to the resultant mixture and after removing the precipitated solids by filtration, the solvent is evaporated to yield a light amber colored oil (Yield: 90%).

Diabetic rat test -33%-100 mg./kg.

What is claimed is:

1. A method of lowering the glucagon level in plasma comprising administering to a mammal in need of such treatment a therapeutically effective amount of a compound of formula I:

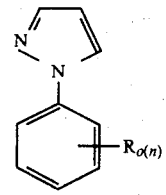

wherein
 $R_o$ is methyl, trifluoromethyl or amino, and
 n is 1 or 2,
or a pharmaceutically acceptable acid addition salt thereof, with the proviso that when n is 2, $R_o$ is methyl, one methyl group being in the 2-position of the phenyl ring and the other methyl group being in the 3- or 4-position of the phenyl ring.

2. A method of lowering the glucagon level in plasma according to claim 1 comprising administering to a mammal a therapeutically effective amount of a compound wherein n is 1 and $R_o$ is trifluoromethyl, methyl in the 2-position of the phenyl ring or amino in the 2-position of the phenyl ring, or a pharmaceutically acceptable acid addition salt thereof.

3. A method of lowering the glucagon level in plasma according to claim 2 comprising administering to a mammal a therapeutically effective amount of a compound wherein n is 1 and $R_o$ is trifluoromethyl.

4. A method of lowering the glucagon level in plasma according to claim 2 comprising administering to a mammal a therapeutically effective amount of the compound of the formula,

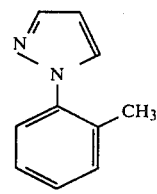

5. A method of lowering the glucagon level in plasma according to claim 3 comprising administering to a mammal a therapeutically effective amount of the compound of the formula,

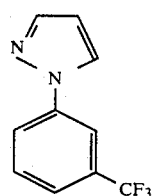

6. A method of lowering the glucagon level in plasma according to claim 3 comprising administering to a mammal a therapeutically effective amount of the compound of the formula,

7. A method of lowering the glucagon level in plasma according to claim 1 comprising administering to a mammal a therapeutically effective amount of the compound of the formula,

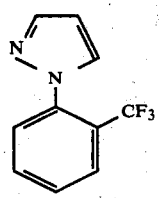

8. A method of lowering the glucagon level in plasma according to claim 1 comprising administering to a mammal a therapeutically effective amount of the compound of the formula,

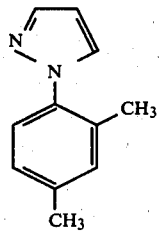

9. A method of lowering the glucagon level in plasma according to claim 2 comprising administering to a mammal a therapeutically effective amount of the compound of the formula,

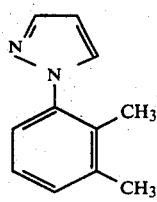

10. A method of lowering the glucagon level in plasma according to claim 1 wherein a compound of formula I is administered in a daily dosage of from about 250 milligrams to about 3000 milligrams.

* * * * *